United States Patent
Harada et al.

(10) Patent No.: US 8,184,286 B2
(45) Date of Patent: May 22, 2012

(54) ATOMIC ABSORPTION SPECTROPHOTOMETER

(75) Inventors: Katsumi Harada, Kyoto (JP); Kazuo Sugihara, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 331 days.

(21) Appl. No.: 12/515,487

(22) PCT Filed: Oct. 31, 2007

(86) PCT No.: PCT/JP2007/001190
§ 371 (c)(1),
(2), (4) Date: May 19, 2009

(87) PCT Pub. No.: WO2008/075445
PCT Pub. Date: Jun. 26, 2008

(65) Prior Publication Data
US 2010/0073675 A1 Mar. 25, 2010

(30) Foreign Application Priority Data

Dec. 18, 2006 (JP) .................................. 2006-339560
Mar. 20, 2007 (JP) .................................. 2007-072410

(51) Int. Cl.
*G01J 3/28* (2006.01)
(52) U.S. Cl. ....................................................... 356/307
(58) Field of Classification Search ......................... None
See application file for complete search history.

(56) References Cited

U.S. PATENT DOCUMENTS 7,221,104 B2 * 5/2007 Lys et al. ...................... 315/291
7,439,497 B2 * 10/2008 Dantus et al. ................. 250/288

FOREIGN PATENT DOCUMENTS

| CN | 1621788 A | 6/2005 |
| JP | 55-058439 A | 5/1980 |
| JP | 60-037518 A | 2/1985 |
| JP | 62-010375 B2 | 3/1987 |
| JP | 2001-153791 A | 6/2001 |

OTHER PUBLICATIONS

Japanese Office Action dated Jul. 5, 2011, issued in corresponding Japanese Patent Application No. 2008-550033.
Written Opinion of the International Searching Authority dated Nov. 27, 2007, issued in corresponding International application No. PCT/JP2007/001190.
Chinese Office Action dated Dec. 7, 2011, issued in corresponding Chiense Patent Application No. 200780044750.7.

\* cited by examiner

*Primary Examiner* — Tu Nguyen
(74) *Attorney, Agent, or Firm* — Sughrue Mion, PLLC

(57) ABSTRACT

An atomic absorption spectrophotometer that memorizes the maximum amount of light of each light source when an transmissivity of each of a plurality of dimmers is largest; computes an appropriate transmissivity of each dimmer for equalizing the amounts of light of the plurality of light sources from the maximum amount of light of each of the light sources; and sets the dimmer's transmissivity to be the appropriate transmissivity.

12 Claims, 4 Drawing Sheets

ATOMIC ABSORPTION SPECTROPHOTOMETER

TECHNICAL FIELD

The present invention relates to an atomic absorption spectrophotometer. More specifically, it relates to an atomic absorption spectrophotometer in which a plurality of light sources, such as a hollow cathode lamp and deuterium lamp, are simultaneously used.

BACKGROUND ART

One type of atomic absorption spectrophotometers in which a plurality of light sources are used has, for example, a function for correcting background absorption with a hollow cathode lamp and deuterium lamp. In such an apparatus, a light beam provided from the hollow cathode lamp and a light beam provided from the deuterium lamp are combined by a beam combiner for example, pass through the space where an analysis sample solution is sprayed (globulized) and atomized, and then are introduced into a spectroscope to become a light beam of necessary wavelength range. After that, the light enters a photoelectric detector to be converted into an electric signal proportional to the light intensity. Furthermore, the electric signal is logarithmically converted. The light beam from the hollow cathode lamp is absorbed by the background and atoms to be analyzed, and the light beam from the deuterium lamp is absorbed by the background (where the absorption by atoms can be ignored because its narrow wavelength range). Since the signal which has been logarithmically converted is proportional to the intensity of absorption, the difference between the signals logarithmically converted from the electric signal proportional to the intensities of both light beams, i.e. amounts of light, is proportional to the intensity of the absorption by atoms, with the influence of the background absorption being eliminated.

In the meantime, a logarithmic conversion circuit for logarithmically converting a signal as previously described can appropriately operate only in a limited signal range. Hence, the conversion accuracy decreases in the case where the signal is excessively small. Given this factor, it is necessary to equalize, as much as possible, the intensity of the electric signal obtained by photoelectrically converting a light beam from the hollow cathode lamp and that of the electric signal obtained by photoelectrically converting a light beam from a deuterium lamp, which are provided into the logarithmic conversion circuit. Therefore, in a conventional apparatus, one of the following three manners is employed: (1) the gains of electric circuits corresponding to each lamp are adjusted in order to equalize the intensities of the electric signals corresponding to both lamps; (2) the electric power to be supplied to each lamp is adjusted in such a manner as to equalize the intensities of the electric signals corresponding to both lamps; and (3) a dimmer apparatus is provided for changing a transmissivity in a stepwise fashion between each lamp and a beam combiner in order to adjust the amount of light of both lamps to equalize the intensities of the electric signals.

If the amount of light from a hollow cathode lamp and that from a deuterium lamp are significantly different, the sensitivity of a photoelectric detector (e.g. a photomultiplier) is adjusted for the lamp having the larger amount of light. Accordingly, the signal to noise ratio (S/N) of the signal of the lamp having the smaller amount of light is deteriorated. Given this factor, a beam combiner has been proposed in which a light amount loss is reduced so that the amounts of light of a hollow cathode lamp and a deuterium lamp can be easily balanced (refer to Patent Document 1 for example).

[Patent Document 1] Japanese Unexamined Patent Application Publication No. S60-37518

DISCLOSURE OF THE INVENTION

Problems to be Solved by the Invention

Any of the aforementioned methods (1) through (3) has a disadvantage. That is, in the case where the gain of the electric circuits corresponding to each lamp is adjusted to equalize the intensities of the electric signals corresponding to both lamps, the gain of the electric circuit of the lamp having the smaller amount of light is increased and the noise is also increased, which deteriorates the measurement result's S/N. In the case where the electric power provided to each lamp is adjusted to equalize the intensities of the electric signals corresponding to both lamps, those lamps might be forced to operate out of their specifications. In such a case, the amount of light becomes unsteady and the lamp's lifetime is shortened. In the case where a dimmer apparatus for changing the transmissivity in a stepwise fashion is provided between each lamp and a beam combiner in order to adjust the amount of light of both lamps to equalize the intensities of the electric signals, although the amounts of light may be equalized with particular lamps, those may not be equalized with other lamps having different amounts of light.

The present invention has been devised to solve the aforementioned problems, and the objective thereof is to provide an atomic absorption spectrophotometer which does not significantly deteriorate the S/N, does not unsteady the lamp's amount of light, does not shorten the lamp's lifetime, and can equalize the amounts of light of plural lamps (or light sources) simultaneously used.

Means for Solving the Problems

The first aspect of the present invention developed to solve the aforementioned problems provides an atomic absorption spectrophotometer including a plurality of light sources and a beam combiner for combining a plurality of light beams emitted from the light sources, including:

a) a plurality of dimmer means whose transmissivity is continuously variable, which are placed on each of the light beam paths between the plurality of light sources and the beam combiner;

b) a memory means for memorizing the maximum amount of light of each light source when the transmissivity of each of the plurality of dimmer means is largest;

c) a computational means for computing an appropriate transmissivity of each dimmer means for equalizing the amounts of light of the plurality of light sources from the maximum amount of light of each of the light sources; and d) a setting means for setting each dimmer means' transmissivity to be the appropriate transmissivity.

In the atomic absorption spectrophotometer according to the first aspect of the present invention, the plurality of light sources may be a deuterium lamp and a hollow cathode lamp.

The second aspect of the present invention developed to solve the aforementioned problems provides an atomic absorption spectrophotometer including: a deuterium lamp; a hollow cathode lamp; and a beam combiner for combining two light beams emitted from these lamps, including:

a) a dimmer means whose transmissivity is continuously variable, which is placed on the light beam path between the deuterium lamp and the beam combiner;

b) a memory means for memorizing the maximum amount of light of each lamp when the transmissivity of the dimmer means is largest;

c) a computational means for computing an appropriate transmissivity of the dimmer means for equalizing the amounts of light of the two lamps from the maximum amount of light of each of the lamps; and d) a setting means for setting the dimmer means' transmissivity to be the appropriate transmissivity.

Effects of the Invention

In each of the atomic absorption spectrophotometers according to the first and second aspects of the present invention, the amounts of light from the light sources (i.e. the hollow cathode lamp and deuterium lamp) are almost equalized by the function of each aforementioned means. This equalization of the amounts of light from plural lamps (or light sources) has advantages such as: it can be applied to a variety of lamps, it has a good S/N, and it functions without unsteadying the lamp's amount of light and shortening the lamp's lifetime. Therefore, it is possible to perform an accurate and efficient atomic absorption spectroscopic analysis.

EXPLANATION OF NUMERALS

1 . . . First Light Source
2 . . . Second Light Source
3 . . . First Dimmer Apparatus
4 . . . Second Dimmer Apparatus (Dimmer Apparatus)
5 . . . Beam Combiner
6, 8 . . . Mirror
7 . . . Measurement Unit
9 . . . Spectroscope
10 . . . Photoelectric Detector
11 . . . Preamplifier
12 . . . Logarithmic Converter
13 . . . Display Unit
14 . . . A/D Converter
15 . . . Controller
16 . . . Memory Unit
17 . . . Appropriate Transmissivity Computation Unit
18 . . . Dimmer Apparatus Drive Unit
19 . . . Drive Mechanism
20 . . . Light Attenuator
31, 32 . . . Optical Filter
33 . . . Quartz Glass
34 . . . Drive Unit
35, 36 . . . Dimmer Element

BEST MODES FOR CARRYING OUT THE INVENTION

In one embodiment of the atomic absorption spectrophotometer according to the first and second aspects of the present invention, the dimmer means may include:

an optical filter having a substantially flat wavelength absorption characteristic and a continuously varied transmissivity; and a drive means for shifting the appropriate area thereof to the position where a light beam from the light source passes through.

In the case of an optical filter whose transmissivity changes along a line (one-dimensionally), the drive means may be composed of a stepping motor and a linear drive unit which includes, for example, a rack and pinion. On the other hand, in the case of an optical filter whose transmissivity changes in a circumferential direction, the drive means man by composed of a stepping motor.

EMBODIMENTS

First Embodiment

Figure 1:
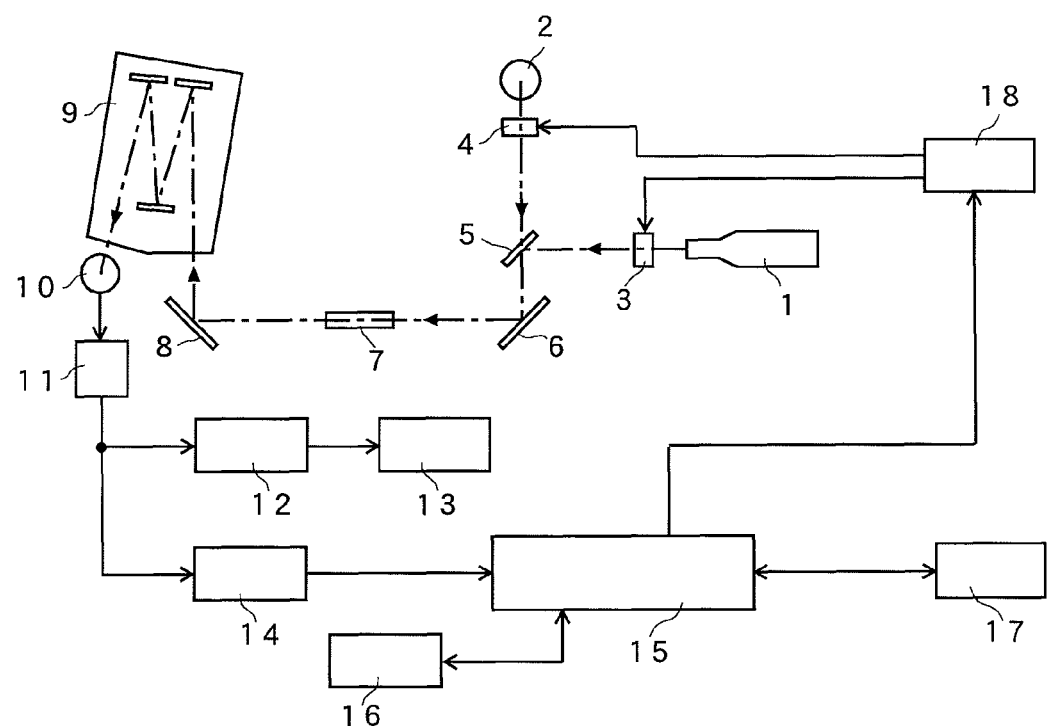
FIG. 1 is a schematic configuration diagram of the atomic absorption spectrophotometer which is an embodiment (the first embodiment) of the present invention.
Figure 2:
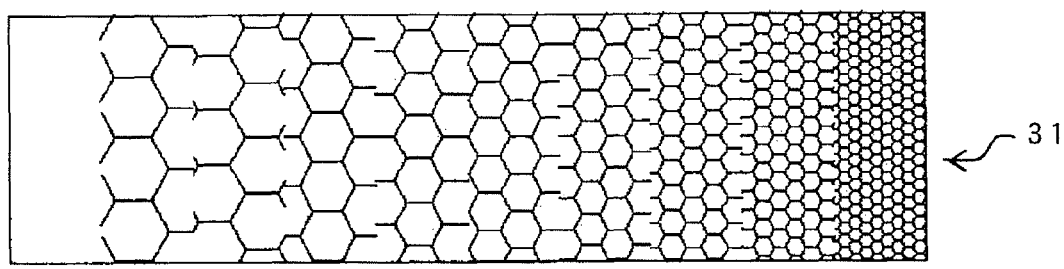
FIG. 2 is a diagram roughly illustrating the optical filter mounted in the dimmer apparatus in the atomic absorption spectrophotometer of the present embodiment.

An atomic absorption spectrophotometer according to an embodiment (the first embodiment) of the present invention will be described with reference to FIGS. 1 and 2. FIG. 1 is a schematic configuration diagram of the atomic absorption spectrophotometer of the first embodiment. FIG. 2 is a diagram roughly illustrating the optical filter mounted in the dimmer apparatus in the atomic absorption spectrophotometer of the first embodiment.

In FIG. 1, a first light source 1 is composed of a hollow cathode lamp and intermittently turned on, for example, at 60 Hz. A second light source 2 is composed of a deuterium lamp and intermittently turned on so that it should be lighted while the first light source 1 is not lighted. A first dimmer apparatus 3 is placed between the first light source 1 and a beam combiner 5, and a second dimmer apparatus 4 is placed between the second light source 2 and the beam combiner 5.

A light beam emitted from the first light source 1 and a light beam emitted from the second light source 2 are combined at the beam combiner 5 which is composed of a half mirror, and then the traveling direction is changed by a mirror 6 to pass through a measurement unit 7 which is a furnace atomization unit. The light further changes its direction by another mirror 8 to be introduced into a spectroscope 9 where only the light of the necessary wavelength range is selected. Then, the light enters a photoelectric detector 10 which is composed of a photomultiplier for example to be converted into an electric current signal. In a preamplifier 11, the electric current signal of the photoelectric detector 10 becomes a voltage signal whose magnitude is proportional to the amount of light. The output signal of the preamplifier 11 has a characteristic that the signal corresponding to the first light source 1 and the signal corresponding to the second light source 2 alternately appear. Hence, these signals are separated by a sampling in synchronization with each lighting period of the first and second light sources 1 and 2. The output signal of the preamplifier 11 is logarithmically converted in a logarithmic converter 12 to be a signal proportional to the absorption of light in the space where a sample solution is globulized and atomized in the measurement unit 7. In these signals, the signal corresponding to the first light source 1 is proportional to the absorption by the background of the aforementioned space and the atoms to be analyzed, and the signal corresponding to the second light source 2 is proportional to the absorption by the background (where the absorption by atoms can be ignored because its narrow wavelength range). A display unit 13 corrects the background absorption, computes the concentration of the atoms to be analyzed, and displays the result.

Each of the first dimmer apparatus 3 and the second dimmer apparatus 4 includes: an optical filter 31 (refer to FIG. 2) whose transmissivity continuously changes one-dimensionally because of the concentration change in the lateral direction of a metal or other materials contained in a substrate made of a glass or other materials; and a stepping motor for linearly moving the optical filter 31 through a rack and pinion. The relationship between the transmissivity of the first dimmer apparatus 3 and the number of drive steps of the stepping motor is expressed by the following formula (1), and the same relationship in the second dimmer apparatus 4 is expressed by the formula (2). These formulas (1) and (2) are stored in a memory unit 16:

$$Ta = Ka \times Na \quad (1)$$

$$Tb = Kb \times Nb \quad (2)$$

where; Ta: transmissivity of the first dimmer apparatus 3; Ka: constant; Na: number of drive steps of the stepping motor of the first dimmer apparatus 3; Tb: transmissivity of the second dimmer apparatus 4; Kb: constant; and Nb: number of drive steps for the stepping motor of the second dimmer apparatus 4. Therefore, in order to set the first dimmer apparatus 3 or the second dimmer apparatus 4 to have the desired transmissivity, a controller 15 drives, through a dimmer apparatus drive unit 18, the stepping motor of the first dimmer apparatus 3 or the second dimmer apparatus 4 by the number of steps determined by the formula (1) or formula (2).

With the measurement unit 7 empty and with the maximum (or approximately 100%) transmissivity of the first dimmer apparatus 3 and the second dimmer apparatus 4, the output voltage of the preamplifier 11 is A/D converted by an A/D converter 14 to obtain the value Pa which corresponds to the first light source 1 and the value Pb which corresponds to the second light source 2. These values Pa and Pb are stored in the memory unit 16 through the controller 15. An appropriate transmissivity computation unit 17 reads out the Pa and Pb values from the memory unit 16 through the controller 15, sets the smaller value as Ps, and computes the appropriate transmissivity T1=(Ps/Pa)×100 for the first dimmer apparatus 3, and the appropriate transmissivity T2=(Ps/Pb)×100 for the second dimmer apparatus 4.

The controller 15 reads out the appropriate transmissivities T1 and T2 that the appropriate transmissivity computation unit 17 has computed, and sets, through the dimmer apparatus drive unit 18, the transmissivity of the first dimmer apparatus 3 to be T1=(Ps/Pa)×100 and the transmissivity of the second dimmer apparatus 4 to be T2=(Ps/Pb)×100. As a result, the value of the output voltage (or A/D converted value) of the preamplifier 11 corresponding to the first light source 1 becomes Pa×(Ps/Pa)=Ps and the value corresponding to the second light source 2 becomes Pb×(Ps/Pb)=Ps. Therefore, the amounts of light of both light sources 1 and 2 are equalized. At this point, the maximum transmissivity which can be set to the first dimmer apparatus 3 and the second dimmer apparatus 4 is not 100% due to the influence of the surface reflection of the optical filter 31 and other factors. However, the error is at most approximately a few %, which hardly influences the performance of the equalization of the amounts of light. The value of Ps is optimized by changing the sensitivity of the photoelectric detector 10 so that the logarithmic converter 12 can accurately perform a logarithmic conversion.

The aforementioned configuration of the atomic absorption spectrophotometer according to the first embodiment realizes the equalization of the amounts of light from the first light source 1 and the second light source 2, which can provide an apparatus that brings about advantages such as: being applicable to many kinds of lamps, having a good S/N, functioning without unsteadying the amount of light of a lamp and shortening the lamp's lifetime, the background absorption being accurately corrected, and being capable of performing an accurate and efficient atomic absorption spectroscopic analysis.

The atomic absorption spectrophotometer according to the first aspect of the present invention is not limited to the aforementioned description of the first embodiment. For example, although the number N of light sources is two in the previously described embodiment, the number N may be more than two. In such a case, the present invention can be applied by arranging N−1 beam combiners 5 in order to combine the light beams from N light sources.

Figure 3:
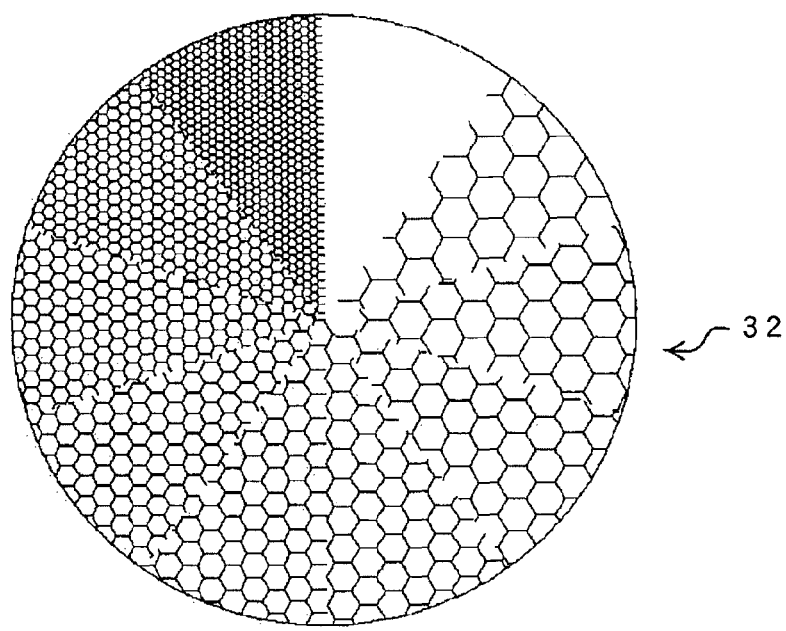
FIG. 3 is a diagram roughly illustrating the optical filter mounted in the dimmer apparatus in the atomic absorption spectrophotometer of a modification example of the present embodiment.

Furthermore, in the aforementioned embodiment, both the first dimmer apparatus 3 and the second dimmer apparatus 4 are composed of an optical filter 31 and a stepping motor for linearly moving the optical filter 31 through a rack and pinion. However, the dimmer apparatus may be replaced by another dimmer apparatus composed of an optical filter 32 (refer to FIG. 3) in place of the optical filter 31 and a stepping motor, without a rack and pinion, for directly moving the optical filter 32 in the circumferential direction. The transmissivity of the optical filter 32 continuously changes in a circumferential direction due to the concentration change in the circumferential direction of a metal or other materials contained in a substrate made of a glass or other materials.

Figure 4:
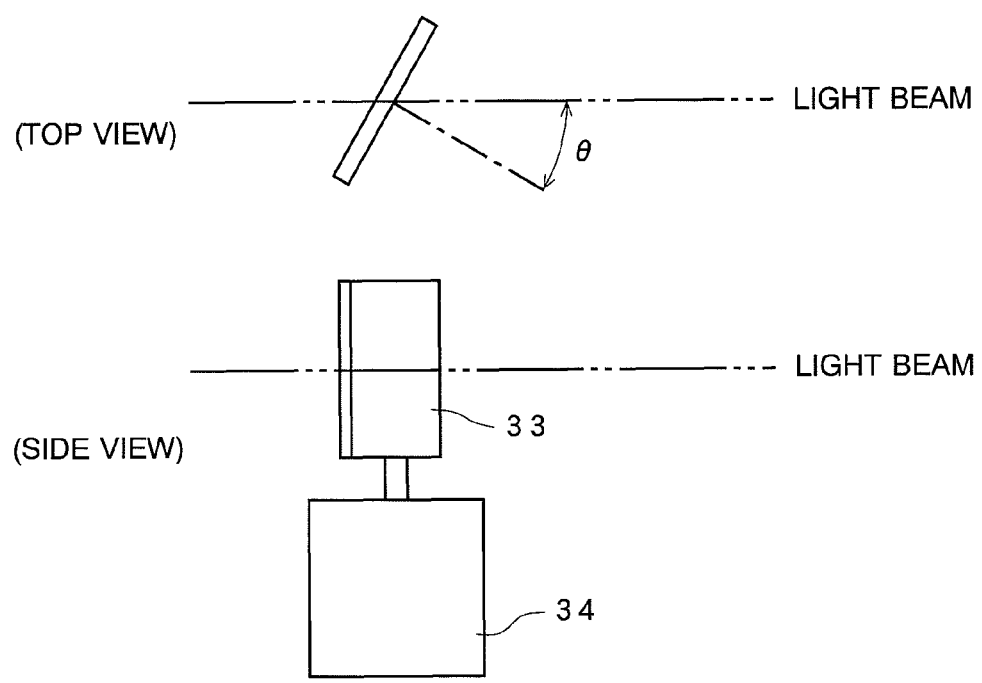
FIG. 4 is a diagram roughly illustrating the dimmer apparatus of a modification example.

Moreover, although both the first dimmer apparatus 3 and the second dimmer apparatus 4 are composed of an optical filter 31 and a stepping motor for linearly moving the optical filter 31 through a rack and pinion in the aforementioned embodiment, the dimmer apparatuses may be replaced by a dimmer apparatus using a substance having a characteristic that the reflectance increases and the transmissivity decreases as the incidence angle increases. In this case, as illustrated in FIG. 4, the dimmer apparatus may be composed of an optical element, which is placed in the optical path at the incident angle $\theta$, having a high transmissivity, such as a quartz glass 33, and a drive motor 34 for controlling the incident angle $\theta$.

Figure 5:
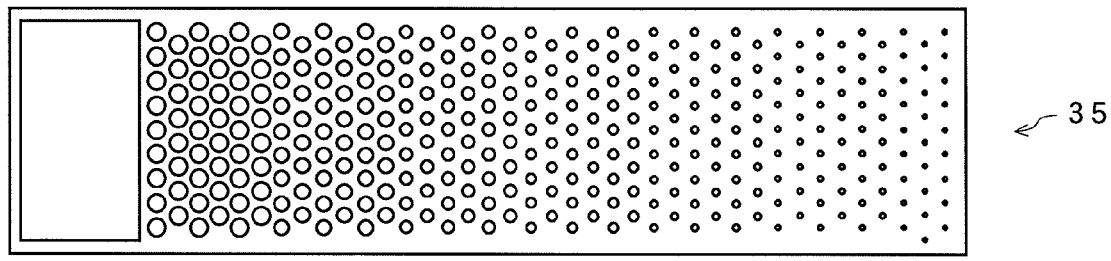
FIG. 5 is a diagram roughly illustrating a linear array type dimmer element mounted in the dimmer apparatus of a modification example.

In addition, although both the first dimmer apparatus 3 and the second dimmer apparatus 4 include an optical filter 31 in the aforementioned embodiment, the dimmer apparatus may be replaced by another dimmer apparatus composed of a dimmer element 35 (refer to FIG. 5), in place of the optical filter 31, in which many small apertures are provided in a thin plate in such a manner that the radius of the apertures or the number of apertures per unit area continuously change in the lateral direction so that the transmissivity may continuously change in the lateral direction.

Furthermore, in the aforementioned embodiment, both the first dimmer apparatus 3 and the second dimmer apparatus 4 are composed of an optical filter 31 and a stepping motor for linearly moving the optical filter 31 through a rack and pinion.

Figure 6:
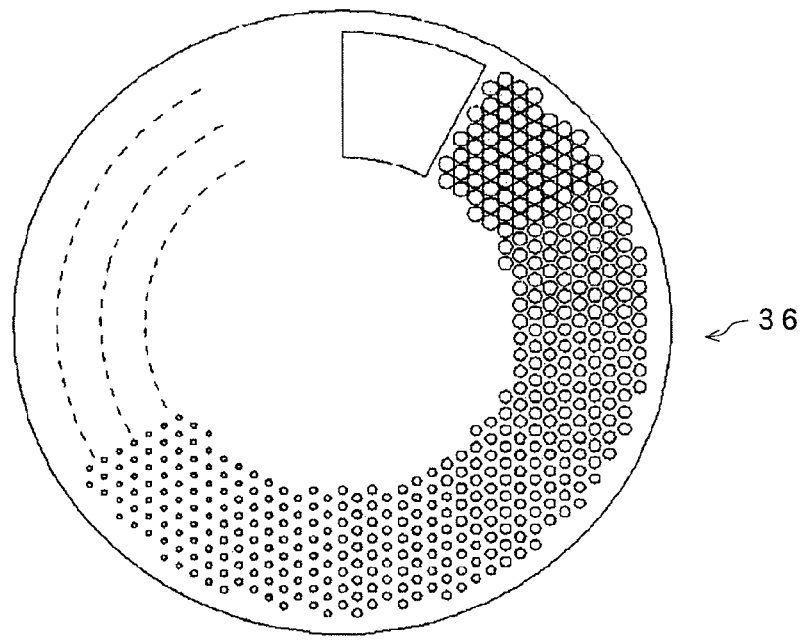
FIG. 6 is a diagram roughly illustrating a circular array type dimmer element mounted in the dimmer apparatus of a modification example.

However, the dimmer apparatus may be replaced by another dimmer apparatus composed of a dimmer element 36 (refer to FIG. 6) in place of the optical filter 31 and a stepping motor, without a rack and pinion, for directly moving the dimmer element 36 in the circumferential direction. The dimmer element 36 is composed of a thin plate in which many small apertures are provided in such a manner that the radius of the apertures and the number of apertures per unit area continuously change in the circumferential direction so that the transmissivity may continuously change in the circumferential direction.

As just described, the atomic absorption spectrophotometer according to the first aspect of the present invention can have a variety of configurations. The first aspect of the invention includes these modification examples.

Second Embodiment

Figure 7:
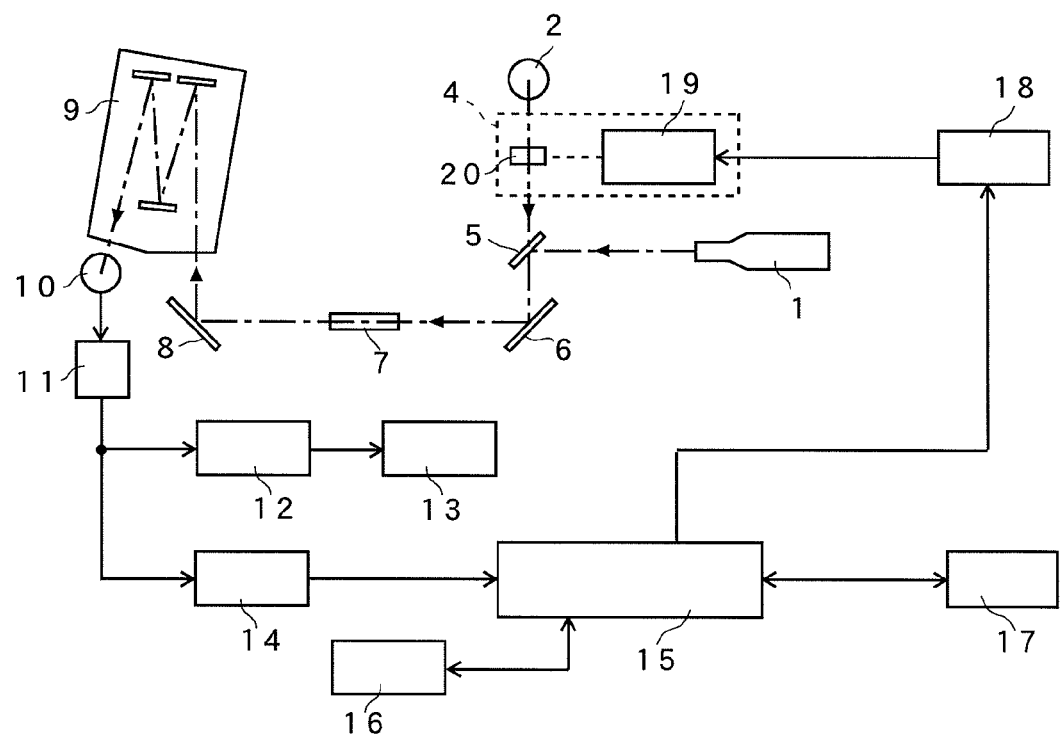
FIG. 7 is a schematic configuration diagram of the atomic absorption spectrophotometer which is another embodiment (the second embodiment) of the present invention.
Figure 8:
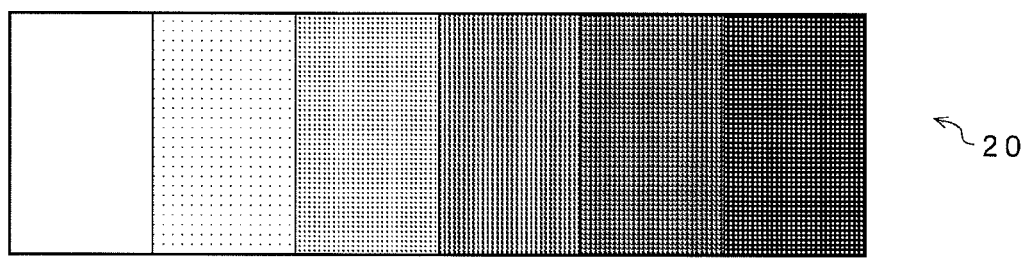
FIG. 8 is a diagram roughly illustrating a light attenuator in the atomic absorption spectrophotometer of the second embodiment.

Next, an atomic absorption spectrophotometer according to another embodiment (the second embodiment) of the present invention will be described with reference to FIGS. 7 and 8. FIG. 7 is a schematic configuration diagram of the atomic absorption spectrophotometer of the second embodiment. FIG. 8 is a diagram roughly illustrating a light attenuator 20 in the atomic absorption spectrophotometer of the second embodiment. The same or corresponding components as in the first embodiment are indicated with the same numerals and the detailed explanations are omitted.

In the configuration of the second embodiment, a dimmer apparatus 4 which corresponds to the second dimmer apparatus 4 in the first embodiment includes: a light attenuator 20 placed on the light beam path between a second light source 2, which is a deuterium lamp, and a beam combiner 5; and a drive mechanism 19 composed of a rack, a pinion, and a stepping motor for laterally moving the light attenuator 20. The light attenuator 20 corresponds to the optical filter in the first embodiment, and, as illustrated in FIG. 8, is composed of a plurality of laterally aligned filters whose transmissivity changes in a stepwise fashion. The relationship between the transmissivity of the light attenuator 20 and the step number of the stepping motor of the drive mechanism 19 is expressed by the following formula (3), which is stored in the memory unit 16:

$$Ta = Ka \times Na \quad (3)$$

where; Ta: transmissivity of the light attenuator 20; Ka: constant; and Na: number of steps of the stepping motor of the drive mechanism 19. Therefore, in setting the light attenuator 20 to have the desired transmissivity, the controller 15 drives, through the dimmer apparatus drive unit 18, the stepping motor of the drive mechanism 19 so that the motor reaches the step number determined by the formula (3).

With the measurement unit 7 empty and with the maximum (or approximately 100%) transmissivity of the light attenuator 20, the output voltage of the preamplifier 11 is A/D converted by an A/D converter 14 to obtain the value Ph which corresponds to the first light source (or hollow cathode lamp) 1 and the value Pd which corresponds to the second light source (deuterium lamp) 2. These values Ph and Pd are stored in the memory unit 16 through the controller 15. The appropriate transmissivity computation unit 17 reads out the Ph and Pd values from the memory unit 16 through the controller 15 and computes the appropriate transmissivity $T3 = (Ph/Pd) \times Kb$ for the light attenuator 20, where Kb: appropriate Ph/Pd magnification.

The controller 15 reads out the appropriate transmissivity T3 that the appropriate transmissivity computation unit 17 has computed, and drives the stepping motor of the drive mechanism 19 through the dimmer apparatus drive unit 18 in order to set the transmissivity of the light attenuator 20 to be $T3 = (Ph/Pd) \times Kb$. As a result, while the value of the output voltage (or A/D converted value) of the preamplifier 11 corresponding to the first light source 1 is maintained at Ph, the value corresponding to the second light source 2 becomes $Pd \times (Ph/Pd) \times Kb = Ph \times Kb$. Therefore, the amounts of light of both light sources 1 and 2 are optimized.

At this point, the transmissivity of the light attenuator 20 does not necessarily correspond to the appropriate transmissivity $T3 = (Ph/Pd) \times Kb$, since the transmissivity changes in a stepwise fashion. In such a case, the transmissivity that is the closest to the appropriate transmissivity T3 is selected and set. In addition, the maximum transmissivity which can be set to the light attenuator 20 is not 100% due to the influence of the surface reflection and other factors. However, the error is at most approximately a few %, which hardly influences the performance of the equalization of the amounts of light. The value of Ph is optimized by changing the sensitivity of the photoelectric detector 10 so that the logarithmic converter 12 can accurately perform a logarithmic conversion.

In the atomic absorption spectrophotometer according to the present embodiment, the improvement of the S/N is achieved for elements with which the amount of light of the first light source 1 is extremely small compared to that of the second light source 2. Such an element includes arsenic, selenium, and stannum. For example, in the case where a hollow cathode lamp of arsenic is used as the first light source 1, the transmissivity of the light attenuator 20 is set to be approximately 11%, and the baseline measurement's standard deviation is approximately 0.0011 Abs.

The aforementioned configuration of the atomic absorption spectrophotometer according to the second embodiment realizes the equalization of the amounts of light of the first light source 1 and the second light source 2, which makes it possible to provide an apparatus which brings about advantages such as: being applicable to many kinds of lamps, having a good S/N, decreasing the lower limit of determination or detection of the analysis, functioning without unsteadying the amount of light of a lamp and shortening the lamp's lifetime, the background absorption being accurately corrected, and being capable of performing an accurate and efficient atomic absorption spectroscopic analysis.

Although the configuration illustrated in FIG. 7 adopts a single beam optical system, it is evident that the present invention can be applied to an atomic absorption spectrophotometer which adopts a double beam optical system. In addition, the measurement unit 7 may be the configuration, in place of a furnace atomization unit, in which a sample solution is atomized by a flame heat. This configuration can also be used in the first embodiment.

Furthermore, in the second embodiment, the light attenuator 20 is linearly moved by the drive mechanism 19 composed of a rack, pinion, stepping motor, and other elements. However, the light attenuator 20 may be replaced by an optical element whose transmissivity changes in a circumferential direction in a stepwise fashion. In this case, the drive mechanism may be composed without the rack and pinion, and designed to move the optical element in the circumferential direction by a stepping motor.

Moreover, in the second embodiment, the light attenuator 20 is composed of a plurality of optical filters whose transmissivity changes in a stepwise fashion. However, the light attenuator 20 may be replaced by the optical filter adopted in the first embodiment; that is, it may be an optical element whose transmissivity continuously and laterally changes because of the concentration change in the lateral direction of a metal or other materials contained in a substrate made of a glass or other materials.

As just described, the atomic absorption spectrophotometer according to the second aspect of the present invention can also have a variety of configurations. The second aspect of the invention includes these modification examples.

The invention claimed is:

1. An atomic absorption spectrophotometer including a plurality of light sources and a beam combiner for combining a plurality of light beams emitted from the light sources, comprising:
   a) a plurality of dimmer means whose transmissivity is continuously variable, which are respectively placed on each of light beam paths between the plurality of light sources and the beam combiner;
   b) a memory means for memorizing a maximum amount of light of each light source when a transmissivity of each of the plurality of dimmer means is largest;
   c) a computational means for computing an appropriate transmissivity of each dimmer means for equalizing amounts of light of the plurality of light sources from the maximum amount of light of each of the light sources; and
   d) a setting means for setting a transmissivity of each of the plurality of dimmer means to be the appropriate transmissivity.

2. The atomic absorption spectrophotometer according to claim 1, wherein the plurality of light sources are a deuterium lamp and a hollow cathode lamp.

3. The atomic absorption spectrophotometer according to claim 1, wherein the computational means sets a smallest one among the maximum amounts of light of the plurality of light sources as a standard amount of light, and computes, from the standard amount of light and the maximum amount of light of each light source, an appropriate transmissivity of the dimmer means corresponding to the light source.

4. The atomic absorption spectrophotometer according to claim 1, wherein the dimmer means includes:
   an optical filter having a substantially flat wavelength absorption characteristic and a continuously varied transmissivity; and
   a drive means for shifting an appropriate area of the optical filter to a position where a light beam from the light source or lamp passes through.

5. The atomic absorption spectrophotometer according to claim 4, wherein the transmissivity of the optical filter changes one-dimensionally, and the drive means includes a stepping motor and a linear drive unit.

6. The atomic absorption spectrophotometer according to claim 5, wherein the drive unit includes a rack and pinion.

7. The atomic absorption spectrophotometer according to claim 4, wherein the transmissivity of the optical filter changes in a circumferential direction, and the drive means includes a stepping motor.

8. An atomic absorption spectrophotometer including: a deuterium lamp; a hollow cathode lamp; and a beam combiner for combining two light beams emitted from these lamps, comprising:
   a) a dimmer means whose transmissivity is continuously variable, which is placed on a light beam path between the deuterium lamp and the beam combiner;
   b) a memory means for memorizing a maximum amount of light of each lamp when a transmissivity of the dimmer means is largest;
   c) a computational means for computing an appropriate transmissivity of the dimmer means for equalizing amounts of light of the two lamps from the maximum amounts of light of each of the lamps; and
   d) a setting means for setting a transmissivity of the dimmer means to be the appropriate transmissivity.

9. The atomic absorption spectrophotometer according to claim 8, wherein the dimmer means includes:
   an optical filter having a substantially flat wavelength absorption characteristic and a continuously varied transmissivity; and
   a drive means for shifting an appropriate area of the optical filter to a position where a light beam from the light source or lamp passes through.

10. The atomic absorption spectrophotometer according to claim 9, wherein the transmissivity of the optical filter changes one-dimensionally, and the drive means includes a stepping motor and a linear drive unit.

11. The atomic absorption spectrophotometer according to claim 10, wherein the drive unit includes a rack and pinion.

12. The atomic absorption spectrophotometer according to claim 9, wherein the transmissivity of the optical filter changes in a circumferential direction, and the drive means includes a stepping motor.

* * * * *